US008770187B2

(12) United States Patent
Murphy

(10) Patent No.: US 8,770,187 B2
(45) Date of Patent: Jul. 8, 2014

(54) AEROSOL DISPENSING DEVICE

(75) Inventor: James Murphy, Millbrook (GB)

(73) Assignee: British American Tobacco (Investments) Limited, London (GB)

( * ) Notice: Subject to any disclaimer, the term of this patent is extended or adjusted under 35 U.S.C. 154(b) by 397 days.

(21) Appl. No.: 12/991,392

(22) PCT Filed: Mar. 26, 2009

(86) PCT No.: PCT/EP2009/053635
§ 371 (c)(1),
(2), (4) Date: Jan. 26, 2011

(87) PCT Pub. No.: WO2009/135729
PCT Pub. Date: Nov. 12, 2009

(65) Prior Publication Data

US 2011/0120455 A1 May 26, 2011

(30) Foreign Application Priority Data

May 6, 2008 (GB) .................................. 0808154.9

(51) Int. Cl.
*A61M 15/06* (2006.01)
*A24F 47/00* (2006.01)

(52) U.S. Cl.
CPC .............. *A61M 15/06* (2013.01); *A24F 47/002* (2013.01)
USPC ............ 128/200.18; 128/200.14; 128/200.24; 128/203.12; 128/203.15

(58) Field of Classification Search
CPC ................... A61M 2015/0021; A61M 11/041; A61M 15/0065; A61M 15/02; A61M 2011/042; A61M 2015/0003; A61M 2015/025; A61M 2016/0021; A61M 2016/0027; A61M 2205/502; A61M 2205/8206; A61M 15/0091; A61M 15/06; A61M 2011/002; A24F 47/002
USPC ............. 128/200.24, 200.14, 200.16, 200.18, 128/200.23, 202.21, 203.12, 203.26, 128/203.27, 204.17; 131/273
See application file for complete search history.

(56) References Cited

U.S. PATENT DOCUMENTS 2,051,030 A 8/1936 Dalinda
3,250,280 A * 5/1966 Hu ................................ 131/173

(Continued)

FOREIGN PATENT DOCUMENTS

EP 0471581 2/1992
JP 54-163419 A 12/1979

(Continued)

OTHER PUBLICATIONS

International Search Report and Written Opinion corresponding to PCT/EP2009/053635 mailed Jul. 6, 2009.

(Continued)

*Primary Examiner* — Annette Dixon
(74) *Attorney, Agent, or Firm* — N W Poulsen; L A Pinol

(57) ABSTRACT

An aerosol dispensing device comprises a tubular body that provides a plenum, a mouthpiece having an outlet, a valve for dispensing fluid from a canister as an aerosol with relatively large and small droplet sizes into the plenum for supply to a user through the mouthpiece, and a baffle arrangement that provides first and second passageways each coupled at one end to the plenum and so configured to receive relatively small and large size droplets in the aerosol respectively, the other end of the first passageway extending to the outlet in the mouthpiece to supply the small size droplets to the user, and the other end of the second passageway being closed to inhibit passage of the large size droplets to the mouthpiece outlet, and containing a absorbent pad to prevent leakage of liquid from the canister. The pad may be pre-loaded with a flavourant.

20 Claims, 5 Drawing Sheets

(56) References Cited

U.S. PATENT DOCUMENTS

| | | | | |
|---|---|---|---|---|
| 4,251,033 | A | 2/1981 | Rich et al. | |
| 4,393,884 | A | 7/1983 | Jacobs | |
| 4,454,877 | A * | 6/1984 | Miller et al. | 128/200.21 |
| 4,655,229 | A * | 4/1987 | Sensabaugh et al. | 131/273 |
| 4,765,347 | A * | 8/1988 | Sensabaugh et al. | 131/273 |
| 4,945,929 | A | 8/1990 | Egilmex | |
| 5,388,594 | A * | 2/1995 | Counts et al. | 131/329 |
| 5,894,841 | A * | 4/1999 | Voges | 128/203.12 |
| 7,188,789 | B2 * | 3/2007 | Schwegler et al. | 239/555 |
| 7,581,540 | B2 * | 9/2009 | Hale et al. | 128/203.27 |

FOREIGN PATENT DOCUMENTS

| | | |
|---|---|---|
| JP | 4-229166 | 8/1992 |
| RU | 2188041 C2 | 8/2002 |
| WO | 9729799 A2 | 8/1997 |

OTHER PUBLICATIONS

International Preliminary Report on Patentability, issued Nov. 9, 2010, for International Patent Application No. PCT/EP2009/053635, filed Mar. 26, 2009.

* cited by examiner

AEROSOL DISPENSING DEVICE

CLAIM FOR PRIORITY

This application is a National Stage Entry entitled to and hereby claims priority under 35 U.S.C. §§365 and 371 to corresponding PCT Application No. PCT/EP2009/053635, filed Mar. 26, 2009, which in turn claims priority to British Application Serial No. GB 0808154.9, filed May 6, 2008. The entire contents of the aforementioned applications are herein expressly incorporated by reference.

FIELD OF THE INVENTION

This invention relates to an aerosol dispensing device for dispensing an aerosol to a user for inhalation, for example a nicotine-containing aerosol.

BACKGROUND

Hitherto, proposals have been made for a device reminiscent of a conventional tobacco-containing cigarette, for inhaling nicotine-containing products. For example U.S. Pat. No. 4,393,884 discloses an inhaler having a generally cylindrical body that receives a canister of pressurised fluid that contains nicotine, which is dispensed for inhalation when a user draws on the device in a manner similar to drawing smoke from a conventional cigarette. U.S. Pat. No. 4,945,929 discloses a generally cylindrical body containing a supply of nicotine and pressurised gas which is mixed in a valve to create an aerosol directed to a mouthpiece for a user. The body of the device includes a baffle arrangement to block the passage of relatively large droplets created in the aerosol and allow only smaller size droplets to pass to the mouthpiece for inhalation. However, a problem with this device is that the larger droplets may undesirably drain from the device in a liquid stream.

Also, the mere use of a nicotine aerosol may not find acceptance by smokers as a substitute for conventional cigarettes that provide tobacco smoke for inhalation, due to the lack of smoke flavour in the nicotine aerosol.

SUMMARY OF THE INVENTION

According to the invention, there is provided an aerosol dispensing device comprising a body that provides a plenum, a mouthpiece, a valve for dispensing a fluid as an aerosol with relatively large and small droplet sizes into the plenum for supply to a user through the mouthpiece, and a baffle arrangement that provides first and second passageways each coupled at one end to the plenum and so configured to receive relatively small and large size droplets in the aerosol respectively, the other end of the first passageway extending to an outlet in the mouthpiece to supply the small size droplets to the user, and the other end of the second passageway being closed to inhibit passage of the large size droplets to the mouthpiece.

A member may be provided to capture the large size droplets within the second passageway, for example an absorbent pad may be located at the other end of the second passageway to capture the large size droplets. The pad may be pre-loaded with a tobacco flavourant in order to improve the acceptability of the nicotine aerosol provided to the user through the mouthpiece.

The body may be generally tubular and thereby reminiscent of a cigarette, with the mouthpiece at one end thereof.

The baffle arrangement may comprise an elongate baffle member within the tubular body extending from the plenum towards the mouthpiece in order to provide the first and second passageways. The baffle member may be generally cylindrical and configured so that the first passageway is between the body and the baffle member and the second passageway is within the baffle member. The tubular member and baffle member may be coaxially arranged.

The baffle member may include side apertures to permit aerosol to flow from the second passageway to the first passageway.

At least one air vent may be provided through the body member to allow external air to be drawn into the aerosol supplied to the mouthpiece.

The valve may be operable to open and supply the aerosol into the plenum in response to a user puffing on the mouthpiece. The valve may include a valve seat in the body, an orifice extending through the valve seat and configured to be supplied with pressurised fluid for forming the aerosol, and a moveable valve member resiliently biased against the valve seat to obturate the orifice and so configured that a pressure reduction caused by a user puffing on the mouthpiece causes the valve member to move away from the valve seat to release pressurised fluid through the orifice.

The valve member may include a flexible diaphragm which may include apertures to allow the passage of aerosol, biased by a compression spring towards the valve seat.

The body may include a chamber to receive the pressurised fluid, which may be held in a replaceable canister.

The pressurised fluid may include nicotine and/or other suitable flavours such as for example a tobacco extract, and the overall dress of the device may generally correspond to that of a conventional tobacco-containing filter cigarette.

BRIEF DESCRIPTION OF THE DRAWINGS

In order that the invention may be more fully understood, an embodiment thereof will now be described by way of illustrative example with reference to the accompanying drawings in which.

DETAILED DESCRIPTION

Figure 1:
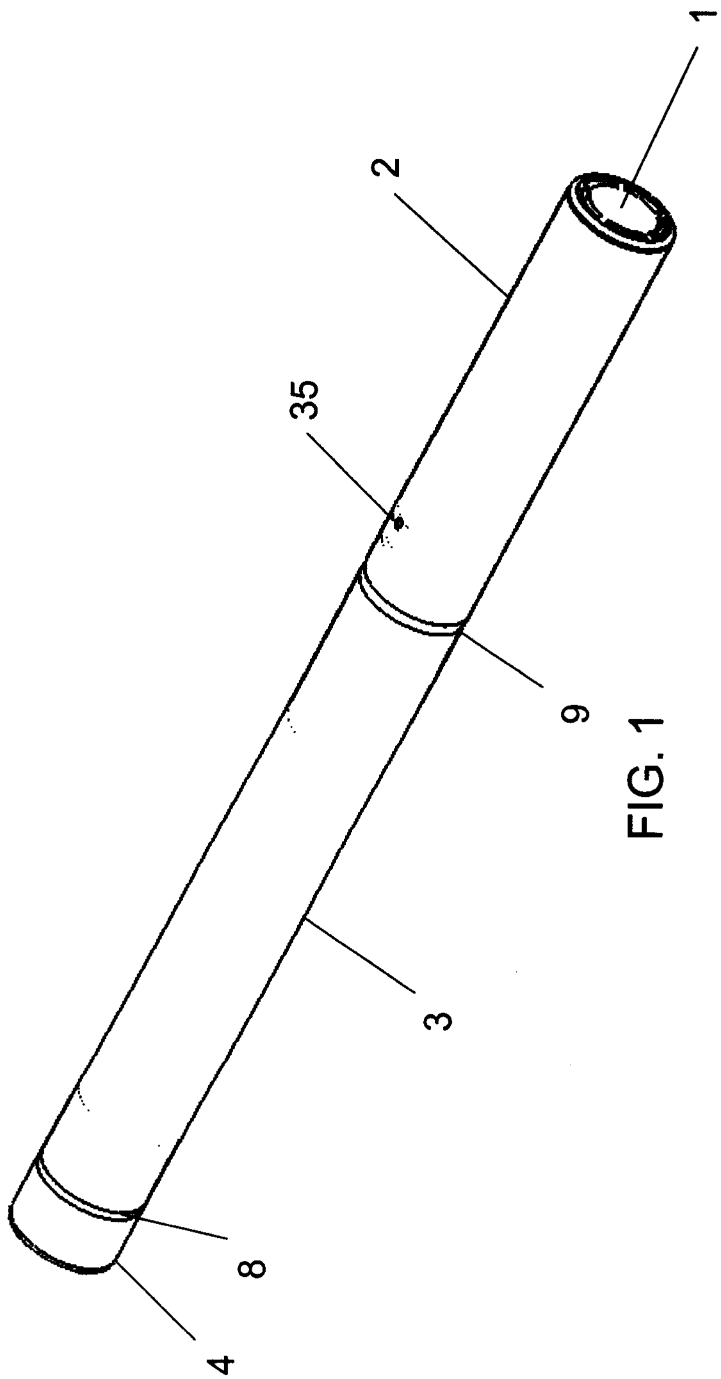
FIG. 1 is a schematic perspective view of an aerosol device.

Referring to FIG. 1, the aerosol device has a generally cylindrical, tubular body of a size and dress generally corresponding to a conventional tobacco-containing cigarette. The device has a mouthpiece member 1, a proximal tubular body member 2 coupled to a distal tubular body member 3 having an end cap 4.

Figure 2:
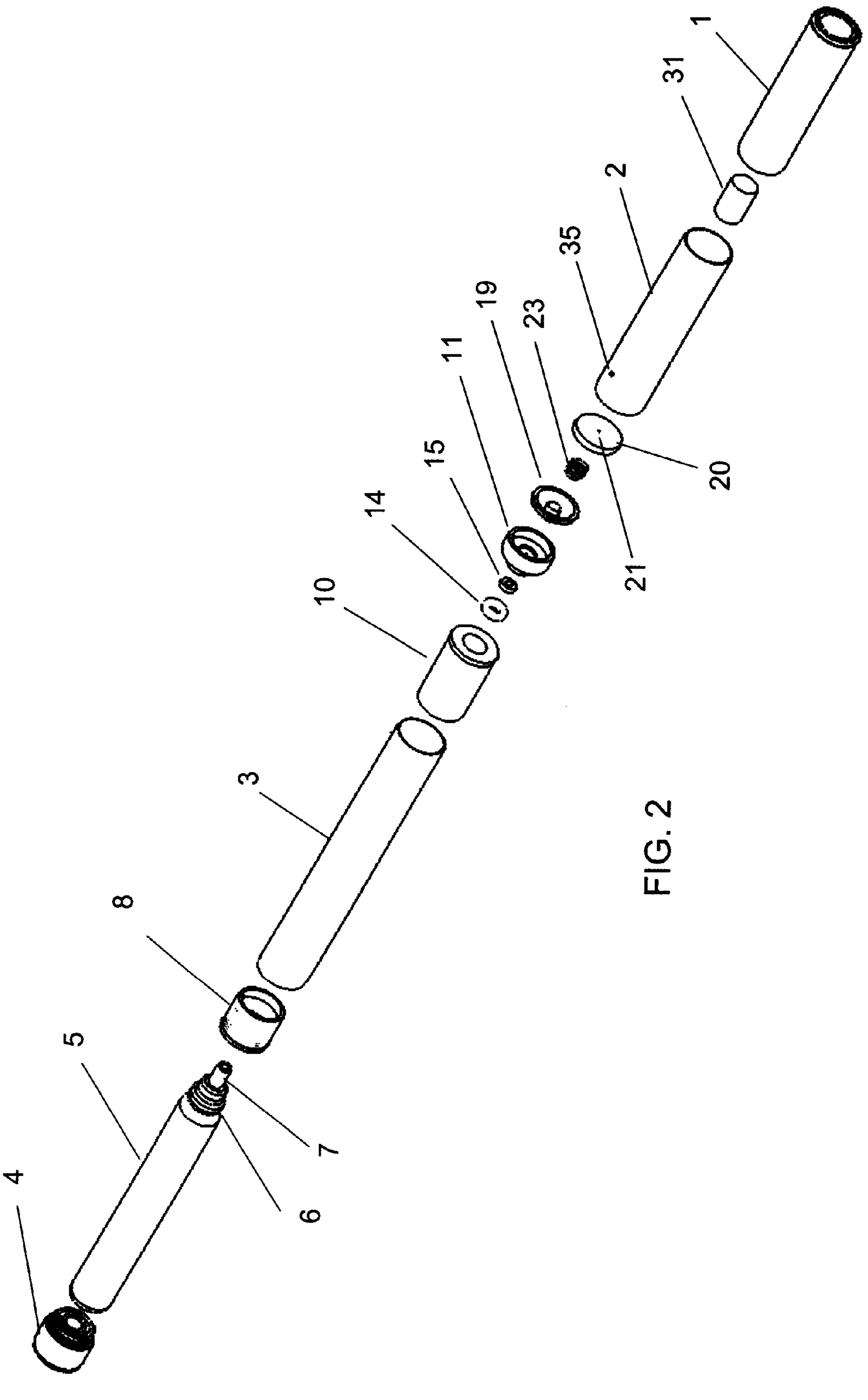
FIG. 2 is an exploded view of the component parts of the device shown in FIG. 1.
Figure 3:
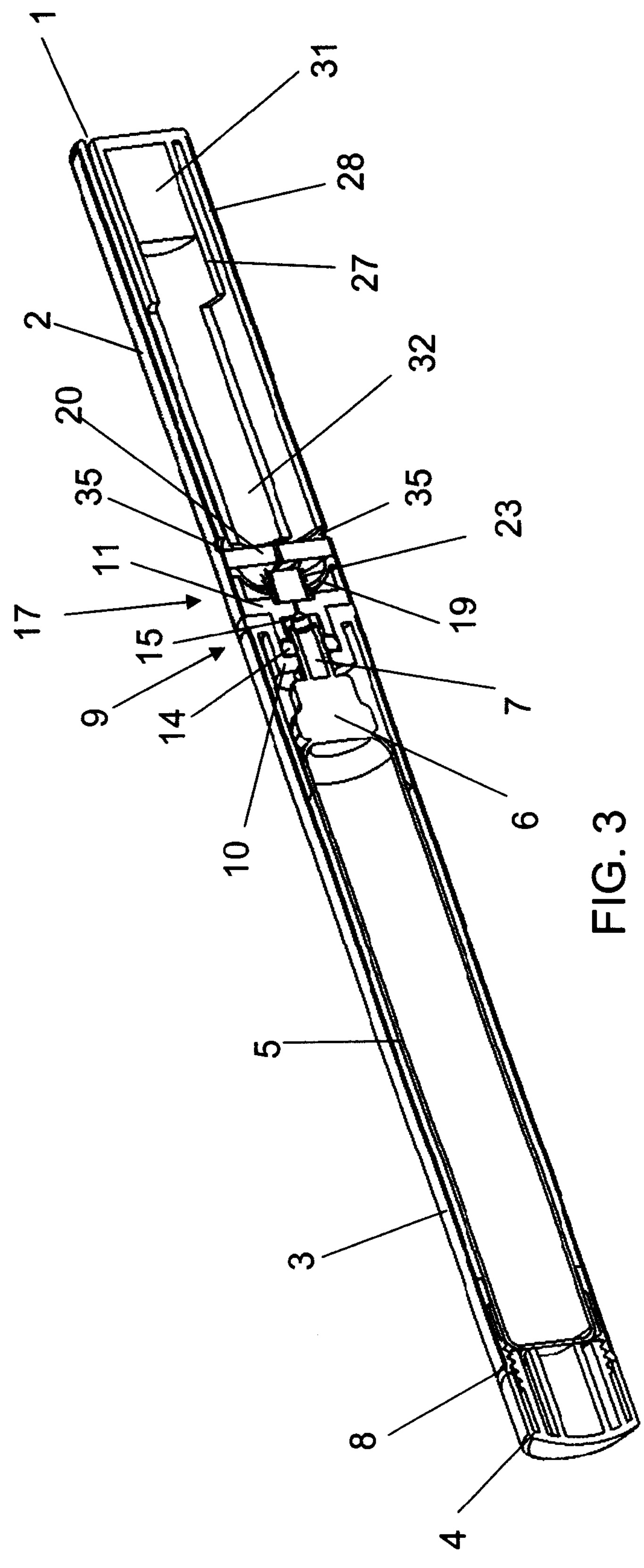
FIG. 3 is a longitudinal sectional view of the device shown in FIG. 1.

As shown in FIGS. 2 & 3, the distal tube 3 of the body member 3 acts as a chamber that receives a canister 5 charged with a pressurised fluid containing a substance to be inhaled by the user e.g. nicotine or a nicotine containing substance or mixture. The canister may be pressurised with a gas such as nitrogen or carbon dioxide or may contain a propellant such as hydrofluroalkane. The canister 5 has an internal valve 6 operated by depression of an inwardly slidable outlet tube 7 to release pressurised fluid from within the canister. The structure of the valve 6 can be conventional, of the type commonly used in pressurised aerosol sprays to provide a continuous rather than a metered flow, and so will not be described in further detail herein. In order to fit the canister into the device, the end cap 4 is removed from a threaded fitment 8 on the far end of the distal tube 3 and the canister 5 is slid into the distal tube so as to abut a canister valve coupling 9 located between the proximal and distal body tubes 2, 3.

Figure 4:
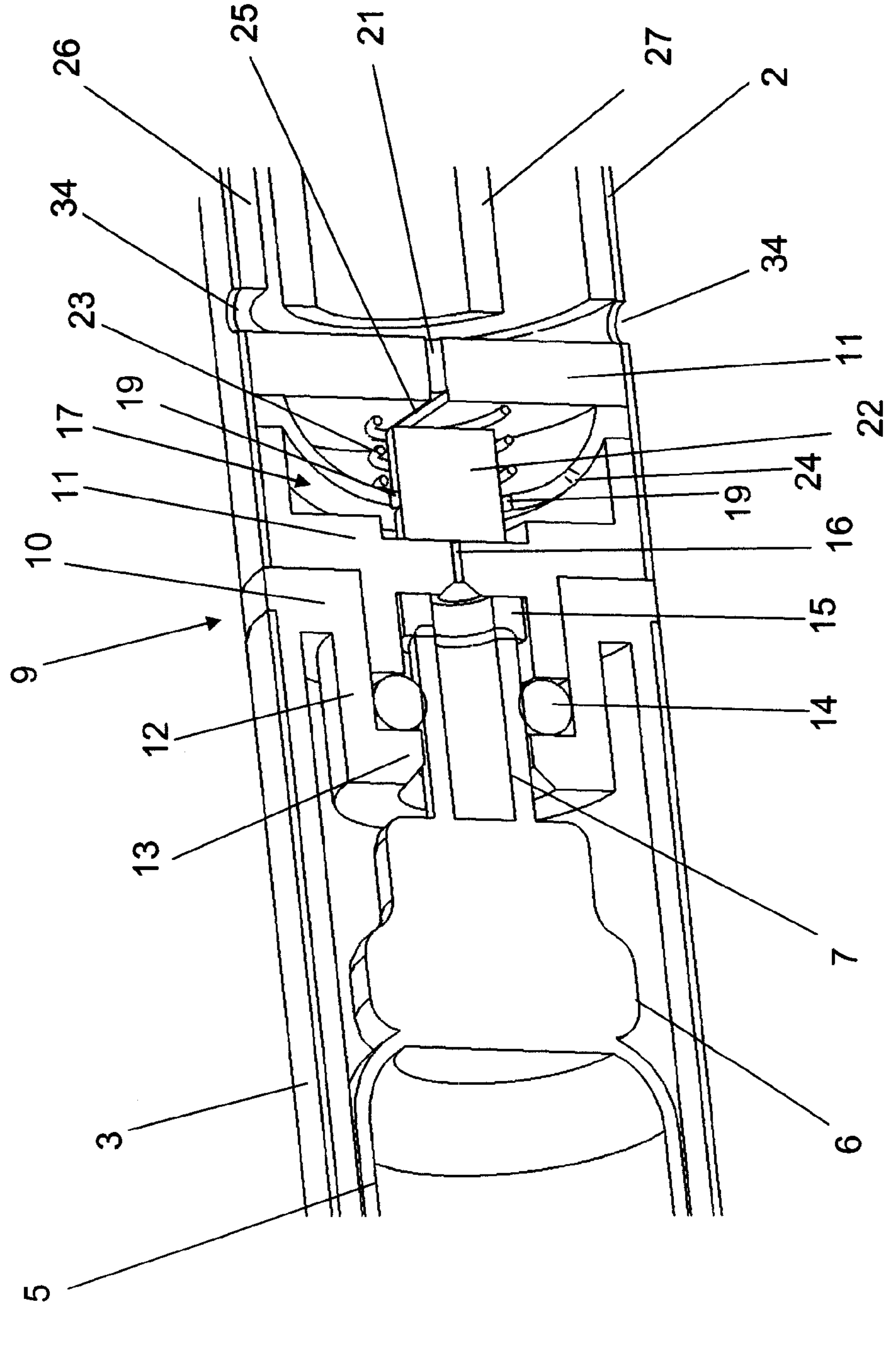
FIG. 4 is an enlarged view of a valve arrangement shown in FIG. 3.

The canister valve coupling 9 includes an inlet part 10 and an outlet part 11 shown in more detail in FIG. 4. The inlet part 10 includes an axial, tubular opening 12 which is formed with an annular flange 13 that captures an O-ring 14. In use, the outlet tube 7 of the canister 5 is inserted into the opening 12 to abut the outlet part 11. As the canister 5 is moved into position and the end cap 4 is closed, the canister valve tube 7 is forced inwardly of the canister 5 to open the valve 6. A pressure seal is formed by the O-ring 14 and also by a gasket 15 within the opening 12. The outlet part 11 includes an axial orifice 16 for supplying pressurised fluid from the canister 5 in the direction of the mouthpiece 1.

Flow of the fluid from the canister is controlled by a valve 17 that comprises a valve seat 18 formed in the outlet part 11 of the valve coupling 9, and an axially moveable valve member 19 that comprises a generally cup-shaped diaphragm which abuts at its periphery a transverse bulkhead 20 that contains an outlet nozzle 21. The valve member 19 also includes a central valve block 22 which is biased by a compression spring 23 against the valve seat 18 so as normally to close the orifice 16.

The valve 17 is configured to open and release pressurised fluid from the canister 5 in response to a user drawing on the mouthpiece, in a manner corresponding to drawing smoke from a conventional tobacco-containing cigarette. The puffing action reduces pressure in the proximal tube 2 of the body and the reduced pressure is communicated through the outlet nozzle 21 such that the pressure of fluid in the canister 5 can act against the force of the compression spring 23 to move the valve block 22 towards mouthpiece, thereby opening the orifice 16 so that fluid from the canister 5 can flow towards the mouthpiece 1 through the orifice 16. The diaphragm 19 includes a plurality of small apertures 24 to allow the fluid to flow through the diaphragm and then pass through the outlet nozzle 21 into the proximal tube part 2. The diameter of the outlet nozzle 21 is configured to produce an aerosol spray of fluid into the proximal tube part 2 of the body.

For example, assuming a pressure of 125 psi in the canister 5 and an orifice diameter of 0.2 mm, the force of the pressurized fluid acting to open the diaphragm 19 is approximately 3 grams. The domed, cup shape of the diaphragm 19 will move to open the valve 17 in response to a user applying negative pressure during inhalation that exceeds the closure force. In this example, if a safety factor of 2 is assumed to keep the outlet closed by means of the spring 23 i.e. approx 6 grams, and with a diaphragm diameter of approximately 8 mm, the negative pressure needed to open the valve 17 is approximately 0.16 psi. This also provides the benefit of a "built-in" natural resistance for the inhalation that approximates to the resistance of a conventional cigarette.

The bulkhead 20 includes a diametric groove 25 aligned with the outlet nozzle 21 so that if the valve block 22 abuts bulkhead 20 whilst the valve is opened, it does not block the outlet nozzle 21 since fluid that passes through the diaphragm apertures 24 can pass along the groove 25 into the nozzle 21.

The mouthpiece 1 comprises a generally tubular member that may be integrally moulded in a plastics material and is configured to be removably fitted into the proximal tube part 2 for interchange. In this example, the mouthpiece 1 is push-fitted into the proximal tube part 2 to assume a configuration shown in FIG. 3.

Figure 6:
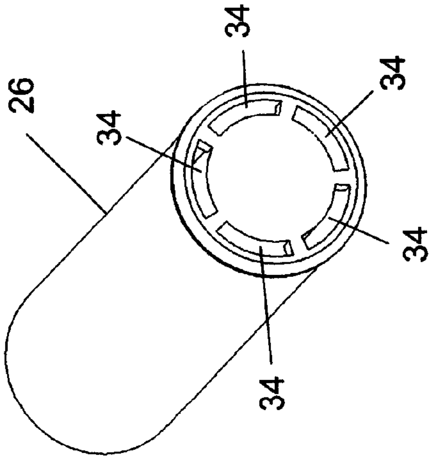
FIG. 6 is a perspective view of a mouthpiece from the other end illustrating the mouthpiece outlet.
Figure 7:
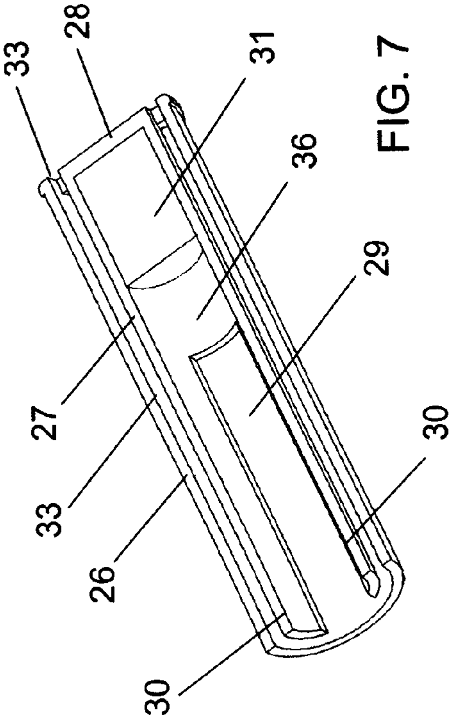
FIG. 7 is a sectional view of the mouthpiece shown in FIG. 5.
Figure 5:
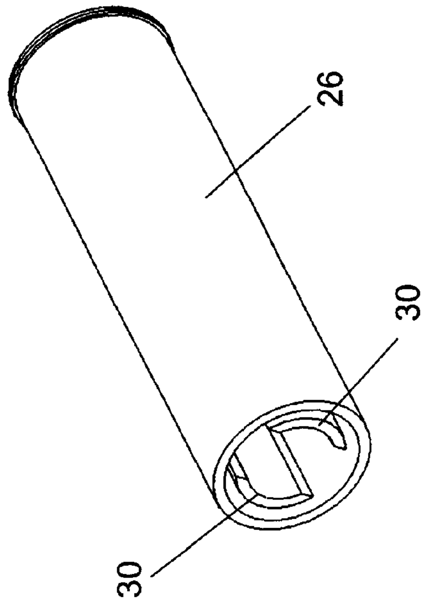
FIG. 5 is a perspective view of the removal mouthpiece of the device from one end.

Referring to FIGS. 5, 6 and 7, the mouthpiece 1 includes a cylindrical outer part 26 and a coaxial generally cylindrical inner part 27. At the proximal end of the mouthpiece, the inner part 27 defines a continuous tube which is closed at the proximal end of the mouthpiece by an end plate 28. Towards the distal end, the inner part 27 includes side apertures 29 disposed between wings 30 that in this example comprise cylindrical extensions of the inner part 27. The inner part 27 thus acts as a baffle member as explained in more detail hereinafter.

A pad 31 of absorbent material is included within the inner part 27 at its closed end 28. The pad 31 may be formed of cellulose acetate material of the kind conventionally used in filters for tobacco-containing cigarettes and may be impregnated with a tobacco flavourant e.g. menthol and/or a flavourant which simulates the aroma of tobacco smoke e.g. by pre-exposing the pad 31 to tobacco smoke. However, it will be appreciated that the pad 31 can be made of other absorbent materials.

As shown in FIG. 3, when the mouthpiece 1 is inserted into the tube 2, a plenum 32 is provided in the tube 2 adjacent to the outlet nozzle 21 for the aerosol produced from fluid in the canister 5. The inner and outer parts 26, 27 of the mouthpiece 1 define first and second passageways extending from the plenum 32 towards the proximal end of the mouthpiece 1. The first passageway 33 is generally cylindrical and provided between the inner and outer parts 26, 27 of the mouthpiece. The first passageway 33 has an inlet that communicates with the plenum 32 and an outlet coupled to outlet apertures 34 in the mouthpiece 1, for supplying aerosol from the plenum 32 to the user in response to the user drawing on the mouthpiece.

Referring to FIG. 3, the proximal tube 2 includes air vents 35 adjacent the bulkhead 20 that allow external air to be drawn into the plenum 32 in response to the user drawing on the mouthpiece 1. The air mixes with the aerosol in the plenum 32 to dilute the aerosol supplied to the user through the passageway 33.

The aerosol emitted by the nozzle 21 will have a range of droplet sizes and the mouthpiece and baffle arrangement 1 is configured so that only relatively small size aerosol droplets reach the user. For example, the nozzle configuration may produce droplets with a size range of 2 μm to 200 μm, although for effective delivery, a relatively small droplet size range of less than 50 μm may desirable, for example in the range of 2.5 μm to 4 μm for lung delivery or 20 μm to 50 μm for buccal delivery. The relatively large sized droplets due to their large mass tend to be projected more longitudinally of the axis of the mouthpiece as compared with the smaller size droplets. The inner part 27 acts as a second passageway 36 that is closed by end plate 28 and captures the relatively large size droplets, which can be absorbed by the pad 31 to prevent a leakage of liquid from the canister passing to the mouthpiece and through openings 34. Furthermore, the dampening of the pad 31 by the aerosol may facilitate release of the flavourant from the pad which will become mixed into the aerosol flow supplied to the user through the first passageway 33. The mouthpiece 1 can be easily removed to allow the mouthpiece to be changed, in particular to allow the pad 31 to be changed when its flavourant becomes expired.

Referring again to FIG. 1, it will be understood that the dress of the aerosol device may be configured to correspond to the appearance of a conventional cigarette, with the end cap 4 corresponding to the ash, the distal tube 3 corresponding to the tobacco rod and the proximal tube 2 corresponding to the filter. However, unlike a conventional cigarette, the device described herein operates without emitting tobacco smoke. The canister may include sufficient pressurised fluid to replicate the smoking of a plurality e.g. twenty conventional tobacco-containing cigarettes, after which the canister may be removed and replaced by unscrewing the end cap 4.

Many modifications and variations of the described example of the invention will be evident to those skilled in the art, which fall within the scope of the claims hereinafter. For example, although the described device is charged with pressurised fluid in the canister 5, the chamber within the distal tube 3 could be a sealed chamber which is directed charged with pressurised fluid through a filling valve. Also, the device need not be tubular in appearance and other body shaped could be used.

The invention claimed is:

1. An aerosol dispensing device comprising:

a body that provides a plenum, a mouthpiece having an outlet, a fluid dispensing valve that dispenses a fluid as an aerosol with relatively large and small droplet sizes into the plenum for supply through the mouthpiece, and a baffle arrangement that provides first and second passageways each coupled at one end to the plenum and configured to receive relatively small and large size droplets in the aerosol respectively, the other end of the first passageway extending to the outlet in the mouthpiece forming a supply passageway for the small size droplets, and the other end of the second passageway forming a closed passageway inhibiting passage of the large size droplets to the mouthpiece outlet.

2. The device according to claim 1, including a member that captures the large size droplets within the second passageway.

3. The device according to claim 2, wherein the member comprises an absorbent pad at the other end of the second passageway.

4. The device according to claim 3, wherein the pad is pre-loaded with a tobacco flavourant.

5. The device according to claim 1, wherein the body is generally tubular with the mouthpiece at one end thereof, and the baffle arrangement comprises an elongate baffle member within the tubular body extending from the plenum towards the mouthpiece outlet and forming the first and second passageways.

6. The device according to claim 5, wherein the baffle member is generally cylindrical and the first passageway is between the body and the baffle member and the second passageway is within the baffle member.

7. The device according to claim 6, wherein the tubular body and the baffle member are coaxially arranged.

8. The device according to claim 5, wherein the mouthpiece and the baffle member are formed as a single unit which is removably mounted on the tubular body.

9. The device according to claim 8, wherein the mouthpiece comprises a tubular outer part with the baffle member being configured within the outer part, whereby the first passageway is formed between the outer part and the baffle member.

10. The device according to claim 1, wherein the baffle member includes side apertures through which aerosol flows from the second passageway to the first passageway.

11. The device according to claim 1, including at least one air vent through the body, the air vent being configured to draw external air into the aerosol supplied to the mouthpiece.

12. The device according to claim 1, wherein the valve is operable to open and supply the aerosol into the plenum in response to a user drawing on the mouthpiece.

13. The device according to claim 12, wherein the valve includes a valve seat in the body, an orifice extending though the valve seat and configured to receive pressurized fluid for forming the aerosol, and a movable valve member resiliently biased against the valve seat to obturate the orifice and so configured that a pressure reduction caused by a user drawing on the mouthpiece causes the valve member to move away from the valve seat to release pressurized fluid through the orifice.

14. The device according to claim 13, wherein the valve member includes a flexible diaphragm.

15. The device according to claim 14, wherein the diaphragm includes apertures configured to allow passage of the aerosol, and is biased by a compression spring towards the valve seat.

16. The device according to claim 1, wherein the plenum is bounded on one side by a bulkhead that includes a nozzle that supplies aerosol from the valve into the plenum.

17. The device according to claim 1, wherein the body includes a receiving chamber that receives pressurized fluid.

18. The device according to claim 17, wherein the receiving chamber is configured to receive a replaceable canister of the pressurized fluid.

19. The device according to claim 1, wherein the device is charged with a fluid that contains nicotine.

20. The device according to claim 1, and having a dress generally corresponding to that of a tobacco containing filter cigarette.

* * * * *